United States Patent [19]

Ildikó Vidra, née Sándor et al.

[11] 4,337,266
[45] Jun. 29, 1982

[54] CYTOSTATIC TERMINALLY BIFUNCTIONAL SUGAR ALCOHOLS PROCESS FOR PREPARING THEM AND PHARMACEUTICAL COMPOSITIONS CONTAINING THEM

[76] Inventors: Ildikó Vidra, née Sándor, 5/c., Budai L.u., 1024 Budapest; László Institoris, 32., Eötvös u., 1067 Budapest, both of Hungary

[21] Appl. No.: 177,948

[22] Filed: Aug. 14, 1980

[30] Foreign Application Priority Data

Aug. 17, 1979 [HU] Hungary .............................. VT 1266

[51] Int. Cl.³ .................. A61K 31/335; C07D 303/22
[52] U.S. Cl. ..................................... 424/278; 549/555
[58] Field of Search .................... 260/348.57, 348.58; 424/278

[56] References Cited

FOREIGN PATENT DOCUMENTS 1668241 2/1971 Fed. Rep. of Germany .

OTHER PUBLICATIONS

Hidvegi et al., Biochem. Pharmacol., (1976), vol. 25(15), pp. 1705-1710.

*Primary Examiner*—Norma S. Milestone
*Attorney, Agent, or Firm*—Karl F. Ross

[57] ABSTRACT

The invention relates to novel anticarcinogenic compounds of formula I,

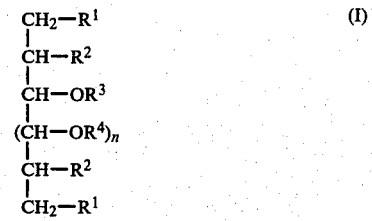

wherein
$R^1$ is halogen
$R^2$ is hydroxy or
$R^1$ and $R^2$ together form an oxygen bridge,
$R^3$ is methyl,
$R^4$ is hydrogen, methyl or acyl,
n is 1 or zero, with the provisos, that in case n is 1 the steric positions of $-R^2$, $OR^3$ and $-OR^4$ groups correspond to dulcitol, mannitol or sorbitol configurations independently of their actual meanings, in case n is zero the steric positions of $-R^2$ and $-OR^3$ groups correspond to xylitol configuration independently of their actual meanings.

The novel compounds can be used as antitumor agents in themselves or formulated as pharmaceutical preparations.

2 Claims, No Drawings

CYTOSTATIC TERMINALLY BIFUNCTIONAL SUGAR ALCOHOLS PROCESS FOR PREPARING THEM AND PHARMACEUTICAL COMPOSITIONS CONTAINING THEM

The invention relates to novel anticarcinogenic compounds of formula I

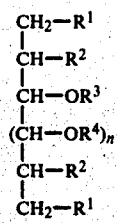

wherein
$R^1$ is halogen,
$R^2$ is hydroxy or
$R^1$ and $R^2$ together form an oxygen bridge,
$R^3$ is methyl,
$R^4$ is hydrogen, methyl or acyl,
n is 1 or zero, with the provisos that where n is 1 the steric positions of $-R^2$, $-OR^3$ and $-OR^4$ groups correspond to dulcitol, mannitol or sorbitol configurations independently of their actual meanings, and in case n is zero the steric positions of $-R^2$ and $-OR^3$ groups correspond to xylitol configuration independently of their actual meanings. The invention also relates to a process for preparing the above compounds and the pharmaceutical compositions containing them.

Those compounds of formula I wherein n is zero correspond to formula IB while those ones wherein n is 1 fall under formula IA.

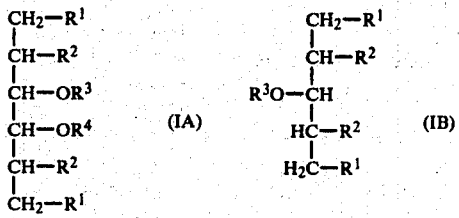

Compounds of formulae IA and IB have not been disclosed in the art as yet. Analogs to compounds of formula IA containing a cyclic ether (a dioxolane ring) at the 3,4-positions are described but the terminal diepoxy and dihalogen derivatives of 3,4-O-isopropylidene hexitols have no antitumor activity [Arzneimittel Forschung, 17, 145–149 (1967)].

It has been found that the cytostatic activity of 1,6-dihalo or 1,2-5,6-dianhydro hexytols and that of 1,6-dihalo and 1,2-4,5-dianhydro xylitol can be modified by transforming the secondary hydroxy groups into ethers by reacting them with lower alkyl groups.

Compounds of formula IA may be prepared by methylating 1,2-5,6-dianhydro hexitols of formula II, with an appropriate methylating agent under proper conditions without damaging the oxirane rings of the starting material. Depending on the reaction conditions either the monomethyl derivatives of formula III or the dimethyl derivatives of formula V are formed. Compounds of formula III, which constitute a smaller group of compounds of formula IA may be transformed into compounds of formula V by methylating them with an appropriate methylating agent, or if desired, they may be transformed to acyl derivatives of formula IV by acylating them with an acylating agent of formula $R^4X$ wherein X represents halogen, preferably bromo, or an acylating agent of formula $(R^4)_2O$. The monomethyl dianhydro hexitols of formula III or acyl derivatives thereof of formula IV or dimethyl dianhydro hexitols of formula V may be transformed to compounds of formula VI by treating them with a hydrohalide or an alkali halide. Compounds of formula VI can be transformed to diepoxy compounds of formulae III, IV and V by reacting them with an appropriate acid displacing agent of basic character. Compounds of formulae III, IV, V and VI fall under formula IA and constitute special subgroups thereof.

Compounds of formula IB may be prepared by methylating 1,2-4,5-dianhydro xylitols of formula VII with an appropriate methylating agent under proper conditions without damaging the oxirane rings of the starting material. The obtained 3-methyl-1,2-4,5-dianhydro xylitols of formula VIII may be transformed into compounds of formula IX by reacting them with a hydrohalide or an alkali halide if desired. Compounds of formula VIII may be prepared by treating a dihalo compound of formula IX with an appropriate acid-displacing agent of basic character. Compounds of formulae VIII and IX fall under formula IB and constitute special subgroups thereof.

It has surprisingly be found that dianhydro hexitols of formula II and dianhydro xylitols of formula VII can be methylated without damaging their oxirane rings if diazomethane, dimethylsulfate or a methylhalide is used as a methylating agent in the absence of water.

(a) If the methylating agent is diazomethane a solution or a suspension of a dianhydro hexitol or a dianhydro xylitol may be treated with same in the presence of a catalyst. The reaction mixture may be treated with diazomethane in the form of gas introduced into the mixture or in the form of a solution dropped therein. Preferred catalysts are fluoroboric acid, boron trifluoride, oxides of alkali metals or alkaline earth metals, aluminum chloride or selenium dioxide; the most preferred catalyst is boron trifluoride etherate.

(b) The methylation may also be carried out by reacting a dianhydro hexitol of formula II or a dianhydro xylitol of formula VII with dimethyl sulfate in the presence of a base under anhydrous conditions. As a base a metal hydride can be used; the preferred base is sodium hydride. Ether-type compounds can be used as solvents; the preferred solvents are the ethers used in the methylation process performed with diazomethane.

(c) Alkyl halides can also be used as methylating agents; preferably methyl iodide or methyl bromide is used and as a catalyst a metal oxide and/or a metal hydride, preferably silver oxide, calcium oxide, strontium oxide, barium oxide and/or hydroxide can be used. The preferred solvents are dimethyl formamide and dimethyl sulfoxide.

Compounds of formulae III and V obtained by methylation and compounds of formula VIII can themselves be used as cytostatic agents but they can also be transformed into other cytostatic sugar alcohol derivatives according to the invention.

In the case where a monomethyl derivative of formula III is treated with an acylating agent of formula $R^4X$ or $(R^4)_2O$ in the presence of an acid binding agent the obtained reaction product is an acyl derivative of formula IV. Any acid binding agent generally used in the organic preparative practice can be employed. The suitable acid binding agents are of organic or inorganic character e.g. tertiary amines like pyridine, picolines, trialkyl amines; alkali or alkaline earth metal carbonates or bicarbonates or phosphates. Preferred acid binding agents are those ones which can easily be removed from the reaction mixture also in the form of their salts formed in the course of the acid binding reaction. Alternatively when e.g. acetic anhydride is used as acylating agent an alkali acetate can also be applied as acid binding agent. With the acid binding agent having only the role of moving the poise of the reaction towards the formation of the acylated products by binding the formed acid, it is not a critical reaction parameter.

Compounds of formulae III, IV, V and VIII can be transformed into compounds of formulae VI or IX by treating them with a hydrohalide or an alkali halide, wherein the halo atom is chloro, bromo or iodo. Two reaction ways are available for this transformation. Either a dianhydro compound is reacted with a concentrated aqueous solution of a haloid acid, or the reaction is carried out under milder conditions by dissolving a dianhydro compound of formulae III, IV, V or VIII in the aqueous solution of an alkali salt of the proper haloid acid, then adding the concentrated solution of a strong acid, e.g. sulfuric acid or perchloric acid to the solution under vigorous stirring the addition being performed so that the reaction mixture remain substantially neutral (cca. pH=6.5-7). The compounds of formulae VI and IX obtained by the above indicated processes fall under formula IB.

If desired, compounds of formulae VI and IX can be transformed into compounds of formulae III, IV, V or VIII by treating them with an acid displacing agent of basic character. Any strong organic or inorganic base can be applied in the above reaction as an acid displacing agent. Preferred organic bases are e.g. alcoholates or alkali or alkaline earth metals, or organic nitrogen-containing bases; preferred inorganic bases are e.g. hydroxides, carbonates or bicarbonates of alkali or alkaline earth metals. The reaction can also be carried out by using anionic ion exchangers in hydroxy form.

The reactions according to invention by which compounds of formulae IA and IB can be prepared from the dianhydro hexitols of formula II or the dianhydro xylitols or formula VII are illustrated hereinbelow; the most characterizing reactants to the single transformations are indicated over the arrows.

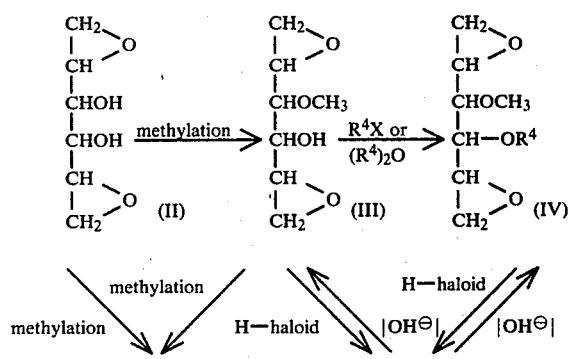

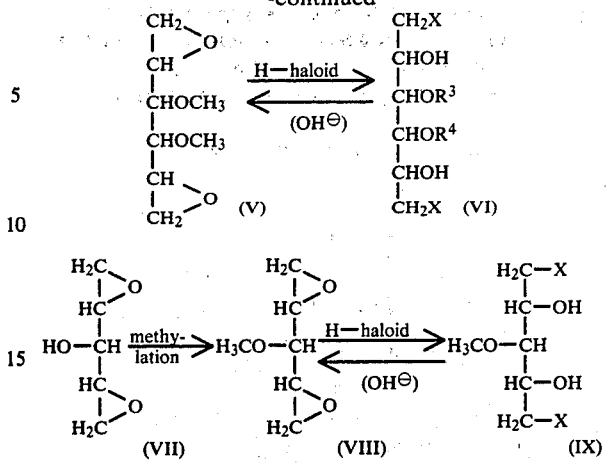

$R^1$ can represent any halogen atom; preferred halogens are chloro, bromo or iodo, the most preferred halogen is bromo.

If $R^4$ does not represent hydrogen or a methyl group, but an acyl group in general, then the alkanoyl groups within the definition of $R^4$ are those having from two to ten carbon atoms, preferably from two to six carbon atoms. These alkanoyl groups can have straight or branched carbon chains and they can be substituted with one or more halogen atoms if desired. If $R^4$ is an aralkanoyl group, it is of from one to ten carbon atoms, preferably of from one to six carbon atoms. The carbon chains of the alkyl groups can be straight or branch chain and an optionally substituted, preferably unsubstituted aryl group of from six to ten carbon atoms is situated at any carbon atom of the carbon chain. Said aryl group is preferably a phenyl group. Preferred aralkanoyl groups are phenyl propionyl and phenyl butyryl groups.

If $R^4$ is an aroyl group that can be substituted or unsubstituted, preferably has six to ten carbon atoms which may be substituted by one or more halogen atoms, nitro, trifluoromethyl, alkyl, phenyl, amino or sulfonyl group, similarly to the aryl parts of the aralkanoyl substituents. A preferred aroyl group is the p-phenylbenzoyl group.

If X is a halogen atom, it can be chloro, bromo or iodo. Haloids can preferably be chlorides, bromides or iodides.

Biological efficiency

Cytopharmacological activity of the compounds of formulae IA and IB, which compounds may be prepared according to the invention, is illustrated by giving the test results obtained testing the compounds listed hereinblow:

1,6-dibromo-1,6-dideoxy-3,4-dimethyl dulcitol (DMDBD),
1,2-5,6-dianhydro-3,4-dimethyl dulcitol (DMDAD),
1,2-4,5-dianhydro-3-methyl-xylitol (MMDAX).

Toxicity tests
LD$_{50}$ values on mice after intraperitoneal administration:
DMDBD     700 mg/kg
DMDAD     680 mg/kg
MMDAX     500 mg/kg
Activity against Walker intramuscular carcinosarcoma Antitumour activity

| | | |
|---|---|---|
| DMDBD | 1 × 50 mg/kg/ip | 80% |
| | 1 × 100 mg/kg/ip | 99% |
| DMDAD | 1 × 50 mg/kg/ip | 55% |
| | 1 × 100 mg/kg/ip | 80% |
| MMDAX | 1 × 100 mg/kg/ip | 90% |
| Activity against S-180 subcutan sarcoma | | |
| DMDBD | 8 × 50 mg/kg/ip | 90% |
| DMDAD | 8 × 50 mg/kg/ip | 80% |
| MMDAX | 8 × 50 mg/kg/ip | 75%. |

Comparative tests carried out on other tumors ($L_{1210}$ leukemia of mice, Yoshida sc. sarcoma, $P_{388}$ i.p. leukemia) gave results similar to those ones given hereinabove; on the basis of these results it has been found that compounds of formulae IA and IB show significant cytostatic activity and their cytostatic effect is superior to that of the basic molecules.

The new anticarcinogenic compounds of formulae IA and IB can be used in therapy in various forms.

Per os: the pure active ingredient without carriers or the pure active ingredient mixed together with auxiliaries generally used in making tablets (e.g. starch, lactose, talc) formulated in the form of tablets.

Intravenously: dissolved in water or in a pharmacologically inert organic solvent (various glycols, etc.).

Intramuscularly: in the form of the above-mentioned solutions or as suspensions.

Intraperitoneally: in the form of the mentioned solutions or as suspensions.

Intracavitalically: the pure active ingredient without carriers or the pure active ingredient in the form of the mentioned solutions or as suspensions.

Locally (in loco): the pure active ingredient is applied on the skin or on the part of the body which was operated without carriers or mixed together with generally used antibacterial agents and compounds used for treatment of wounds (sulfonamides, corticoids, vitamines, etc.).

The preferred active ingredient contents in various preparations:

| | |
|---|---|
| Solution | 1-10% |
| Suspension | 1-70% |
| Tablet | 20-90%. |

The preparation and formulation of the anticarcinogenic compounds according to the invention are illustrated by the following examples.

EXAMPLE 1

1,2-5,6-Dianhydro-3-methyl-dulcitol and 1,2-5,6-dianhydro-3,4-dimethyl-dulcitol 12 g (0.082 moles) of 1,2-5,6-dianhydro dulcitol were suspended in 1500 ml anhydrous ether and diazomethane gas was introduced into the reaction mixture under stirring. When the etheric suspension was saturated to diazomethane, several drops of etheral solution of boron trifluoride etherate were added to the reaction mixture with simultaneous permanent introducing of diazomethane. The addition of boron trifluoride etherate solution was always repeated when the reaction mixture became saturated to diazomethane. When the starting 1,2-5,6-dianhydro dulcitol was completely transformed, saturated aqueous solution of sodium bicarbonate was added to the reaction mixture in an amount sufficient for decomposing the whole amount of the added boron trifluoride etherate, then the reaction mixture was stirred for half an hour and dried over combusted sodium carbonate. The etheral solution was filtered and evaporated, then the residue was taken to a silica gel chromatography column having a volume of twentyfold of the residue and was eluated with a 1 to 1 mixture of benzene and ethyl acetate. Fractions containing the title compounds were evaporated to dryness.

4 g (30.48%) of 1,2-5,6-Dianhydro-3-methyl dulcitol were obtained in the form of colorless oil. $R_f$ is 0.47 (using 1 to 1 mixture of benzene and ethyl acetate).

6 g (42.83%) of 1,2-5,6-Dianhydro-3,4-dimethyl dulcitol were obtained in the form of white crystals. Melting point is 38°–40° C. (crystallized from hexene); $R_f$ is 0.75 (using 1 to 1 mixture of benzene and ethyl acetate).

EXAMPLE 2

1,2-5,6-Dianhydro-3,4-dimethyl dulcitol 12 g of 1,2-5,6-Dianhydro dulcitol were methylated with diazomethane following the procedure described in Example 1. Methylation was finished when the 1,2-5,6-dianhydro-3-methyl dulcitol formed in the first step of reaction transformed completely into 1,2-5,6-dianhydro-3,4-dimethyl dulcitol. The reaction mixture was worked up as described in Example 1. Yield: 77.1%. $R_f$ is 0.75 (using the same solvent mixture as in Example 1).

EXAMPLE 3

1,2-5,6-Dianhydro-3,4-dimethyl dulcitol 5 g (0.031 moles) of 1,2-5,6-Dianhydro-3-methyl-dulcitol were methylated with diazomethane following the procedure described in Example 1, 4.0 g of the named compound were obtained, the melting point of which is 38°–40° C. Yield: 75%. $R_f$ is 0.75 (using the same solvent mixture as in Example 1).

EXAMPLE 4

1,2-5,6-Dianhydro-3-methyl-4-acetyl dulcitol 1.6 g (0.01 moles) of 1,2-5,6-Dianhydro-3-methyl dulcitol were dissolved in 25 ml dry benzene and 1.4 ml of dry triethyl amine was added to the solution under stirring. The reaction mixture was then heated to 45° C. and a solution of 0.78 g dry acetyl chloride in 3 ml dry benzene was dripped into it over an hour under stirring and keeping the mixture at the same temperature. The reaction mixture was stirred at 45° C. for 30 minutes, then the precipitate was filtered and washed with benzene. The combined benzene extracts were evaporated in vacuo. The residual syrup was taken to a silica gel chromatography column having a volume of thirtyfold of the residues and was eluted with a 95 to 5 mixture of benzene and ethyl acetate. Fractions containing the title compound were evaporated to dryness. 1.3 g of the named compound were obtained in the form of colorless oil. Yield: 63%. $R_f$ is 0.77 (using the same solvent mixture as in Example 1).

EXAMPLE 5

1,2-5,6-Dianhydro-3-methyl-4-benzyl dulcitol 1.6 g of 1,2-5,6-Dianhydro-3-methyl dulcitol were dissolved in 25 ml dry benzene and 1.4 ml dry triethyl amine was added to the solution under stirring. The reaction mixture was then heated to 45° C. and a solution of 1.4 g dry benzoyl chloride in 5 ml dry benzene was dripped into it over an hour under stirring and keeping the mixture at the same temperature. The reaction mixture was stirred at 45° C. for 30 minutes, then the precipitate was filtered and washed with benzene. The combined benzene extracts were evaporated in vacuo. The residual syrup was taken to a silica gel chromatography column having a volume of thirty times that of the residue and was eluted with a 95 to 5 mixture of benzene and ethyl acetate. The fractions containing the named compound were evaporated to dryness. 1.72 g of the named compound were obtained in the form of colorless oil. Yield: 65%. $R_f$ is 0.88 (using the same solvent mixture as in Example 1).

EXAMPLE 6

1,2-5,6-Dianhydro-3-methyl-4-α-phenylbutyryl dulcitol 1.6 g of 1,2-5,6-Dianhydro-3-methyl dulcitol were dissolved in 25 ml dry benzene and 1.4 ml dry triethyl amine were added thereto under stirring. Then a solution of 1.82 g -phenylbutyryl chloride in 5 ml dry benzene was dropped into the reaction mixture over an hour at 45° C. under stirring. When the dropping was finished the reaction mixture was still being stirred for half an hour at 45° C. then the precipitate formed was filtered and washed with benzene. The combined benzene solutions were evaporated in vacuo. The residual syrup was taken to a silica gel chromatography column having a volume of thirty times that of the residues and was eluted with a 95 to 5 mixture of benzene and ethyl acetate.

Fractions containing the named compound were evaporated to dryness. 1.4 g of the named compound were obtained in the form of colorless oil. Yield: 39%. $R_f$ is 0.92 (using the same solvent mixture as in Example 1).

EXAMPLE 7

1,2-5,6-Dianhydro-3,4-dimethyl dulcitol 8.78 g of sodium hydride (in the form of a 55% oil suspension) were washed three time with 400 ml portions of anhydrous ether, then it was introduced to 400 ml anhydrous ether and together with 6.2 g of 1,2-5,6-dianhydro dulcitol were stirred for an hour at room temperature. Then 40 drops of dry isopropanol were added to the reaction mixture and 16 ml dimethyl sulfate was dropped into it over two hours. The reaction mixture was being stirred further for 72 hours, then 40 ml anhydrous methanol was added carefully under stirring followed by 100 ml water. The reaction mixture was dripped into the mixture of 5000 ml ethyl acetate and 500 g anhydrous sodium carbonate under vigorous stirring. After being stirred for half an hour the reaction mixture was filtered, the solution was dried over anhydrous sodium sulfate and evaporated. The residual syrup was taken to a silica gel chromatography column having a volume of thirtyfold of the residue and was eluated with a 1 to 1 mixture of benzene and ethyl acetate. Fractions containing the named product were evaporated to dryness and the crystalline residue was recrystallized from hexane. 2.9 g of the named compound were obtained having a melting point of 38°-40° C. Yield: 40%. $R_f$ is 0.75 (using the same solvent mixture as in Example 1).

EXAMPLE 8

1,2-5,6-Dianhydro-3,4-dimethyl dulcitol 4.8 g of 1,2-5,6-Dianhydro dulcitol were dissolved in 24 ml dry dimethyl formamide, then 24 ml dioxane, 24 g barium oxide and 8.7 ml methyl iodide were added under stirring and the mixture was stirred for half an hour at 30° C. The reaction mixture was filtered and the solution was mixed with 40 ml ethyl acetate. Ethyl acetate was decanted from the oily part and the oil was washed twice with 10 ml portions of ethyl acetate. The combined ethyl acetate solutions were evaporated and the residue was taken to a silica gel chromatography column having a volume of thirty times that of the residue and was eluted with a 1 to 1 mixture of benzene and ethyl acetate. Fractions containing the named product were evaporated and recrystallized from hexane. The weight of the obtained product was 2.0 g. Yield: 35.8%; melting point: 38°-40° C.

EXAMPLE 9

1,2-5,6-Dianhydro-3-methyl-D-mannitol and 1,2-5,6-dianhydro-3,4-dimethyl-D-mannitol 12 g (0.082 moles) of 1,2-5,6-Dianhydro-D-mannitol were suspended in 1500 ml dry ether and diazomethane gas was introduced into the reaction mixture under stirring. When the etheral suspension was saturated to diazomethane, several drops of boron trifluoride etherate etheral solution were added to the reaction mixture with simultaneous permanent diazomethane gas introducing. Addition of boron trifluoride etherate solution was always repeated when the reaction mixture became saturated to diazomethane. When the starting 1,2-5,6-dianhydro-D-mannitol transformed completely, a saturated aqueous solution of sodium bicarbonate was added in an amount sufficient to decompose the entire amount of boron trifluoride etherate, the reaction mixture was stirred for half an hour then was dried over combusted sodium bicarbonate. The etheral solution was filtered, evaporated and the residue was taken to a silica gel chromatography column having a volume of thirty times that of the residue and was eluted with a 1 to 1 mixture of benzene and ethyl acetate. Fractions containing the named compounds were evaporated to dryness. 3.5 g of 1,2-5,6-dianhydro-3-methyl-D-mannitol were obtained in the form of colorless oil. Yield: 26.7%. $R_f$ is 0.43 (using the same solvent mixture as in Example 1).

1,2-5,6-Dianhydro-3,4-dimethyl-D-mannitol was obtained as 4.9 g of colorless oil. Yield: 35%. $R_f$ is 0.74 (using the same solvent mixture as in Example 1).

EXAMPLE 10

1,2-5,6-Dianhydro-3,4-dimethyl-D-sorbitol 12 g (0.082 moles) of 1,2-5,6-Dianhydro-D-sorbitol were suspended in 1500 ml anhydrous ether and diazomethane gas was introduced into the reaction mixture under stirring. When the etheral solution was saturated with diazomethane, several drops of boron trifluoride etherate etheral solution were added to the reaction mixture with simultaneous permanent diazomethane gas introducing. Addition of boron trifluoride was always repeated when the reaction mixture became saturated to diazomethane. When the monomethyl compound formed in the first step of the reaction transformed to compound dimethyl saturated aqueous solution of sodium bicarbonate was added to the reaction mixture in an amount sufficient for decomposing the whole amount of the added boron trifluoride etherate, the reaction mixture was stirred for half an hour and dried over combusted sodium carbonate. The etheral solution was filtered, evaporated and the residue was taken to a silica gel chromatography column havng a volume of twenty times that of the residue and was eluated with a 1 to 1 solution of benzene and ethyl acetate. Fractions containing the named product were evaporated to dryness. 4.8 g of 1,2-5,6-dianhydro-3,4-dimethyl-D-sorbitol were obtained in the form of colorless oil. Yield: 33.6%. $R_f$ is 0.74 (using the same solvent mixture as in Example 1).

EXAMPLE 11

1,2-5,6-Dianhydro-3-methyl xylitol 20 g (0.17 moles) of 1,2-4,5-Dianhydro xylitol was dissolved in 1500 ml dry ether and the solution were saturated with diazomethane gas under stirring at room temperature. Then several drops of boron trifluoride etherate etheral solution were added to the reaction mixture with simultaneous permanent diazomethane gas introducing. Addition of boron trifluoride etherate solution was always repeated when the reaction mixture became saturated to diazomethane. When the starting 1,2-5,6-dianhydro xylitol transformed completely, saturated aqueous solution of sodium bicarbonate was added to the reaction mixture in an amount sufficient for decomposing the whole amount of added boron trifluoride etherate, the reaction mixture were stirred for half an hour and dried over combusted sodium carbonate. The filtered clear solution was evaporated and the residue was distilled in vacuo.

15 g of the named compound was obtained in the form of colorless oil. Boiling point: 48° C./1.5 Hgmm. Yield: 67%.

EXAMPLE 12

1,5-Dibromo-1,5-dideoxy-3-methyl xylitol 1 g (0.0077 moles) of 1,2-5,6-Dianhydro-3-methyl xylitol was dissolved in 2 ml acetone and the solution was dripped at a temperature below 0° C. under stirring into 6 ml hydrobromic acid cooled below 0° C., and the mixture was stirred for half an hour at a temperature below 0° C. The pH of the solution was adjusted to 6 by adding sodium bicarbonate. The formed precipitate was filtered and mixed without drying with 50 ml dichloro ethane. The dichloroethane was dried ove combusted sodium sulfate, concentrated to cca. 10 ml and hexane was added, while it became to be turbid. The product precipitated by cooling was filtered and recrystallized from 1 to 1 mixture of dichloro ethane and hexane. 1.4 g of the named product were obtained in the form of colorless crystals. Melting point: 78°–80° C. Yield: 62%. $R_f$ is 0.59 (using the same solvent mixture as in Example 1).

EXAMPLE 13

1,5-Dichloro-1,5-dideoxy-3-methyl xylitol 1 g (0.0077 moles) of 1,2-5,6-Dianhydro-3-methyl xylitol was dissolved in 2 ml acetone and the solution was dripped at a temperature below 0° C. under stirring into 8 ml concentrated hydrochloric acid solution cooled below 0° C. The reaction mixture was stirred for half an hour at a temperature below 0° C. The solution was evaporated in vacuo and the residual oil was taken to a silica gel chromatography column having a volume of twentyfold of the residue and was eluated with a 1 to 1 mixture of benzene and ethyl acetate. Fractions containing the named product were combined and evaporated. 0.8 g of the named compound were obtained in the form of a colorless oil. $R_f$ is 0.52 (using a 1 to 1 mixture of benzene and ethyl acetate as a solvent). Yield: 51%.

EXAMPLE 14

1,5-Diiodo-1,5-dideoxy-3-methyl xylitol 1 g (0.0077 moles) of 1,2-5,6-Dianhydro xylitol was dissolved in 2 ml acetone and the solution was dripped at a temperature below 0° C. under stirring into 8 ml concentrated hydroiodic acid cooled below 0° C. The reaction mixture was stirred for half an hour, the formed crystals were filtered off and recrystallized from ethyl acetate. 1.5 g of the named compound were obtained in the form of colorless crystals. Melting point: 105°–106° C. Yield: 50.5%.

The following eight examples are given in the form of a table for the sake of better lucidity. The end-product were prepared as described in the previous example. The table contains all essential and characterizing data.

TABLE

| | Starting material | | | Product | | | | |
|---|---|---|---|---|---|---|---|---|
| Example | name | amount (g) | Halogenating agent | name | amount (g) | yield (%) | m.p. (°C.) | $R_f^x$ |
| 15 | 1,2-5,6-dianhydro-3-methyl dulcitol | 1 | HBr | 1,6-dibromo-1,6-dideoxy-3-methyl dulcitol | 1.05 | 52 | 130–1 | 0.42 |
| 16 | 1,2-5,6-dianhydro-3-methyl dulcitol | 1 | HCl | 1,6-dichloro-1,6-dideoxy-3-methoxy dulcitol | 0.71 | 49 | 136 | 0.38 |
| 17 | 1,2-5,6-dianhydro-3-methyl dulcitol | 1 | HI | 1,6-diiodo-1,6-dideoxy-3-methoxy dulcitol | 1.4 | 54 | 132 | 0.46 |
| 18 | 1,2-5,6-dianhydro-3,4-dimethyl dulcitol | 1 | HBr | 1,6-dibromo-1,6-dideoxy-3,4-dimethyl dulcitol | 1.37 | 71 | 160 | 0.8 |
| 19 | 1,2-5,6-dianhydro-3,4-dimethyl dulcitol | 1 | HI | 1,6-diiodo-1,6-dideoxy-3,4-dimethyl dulcitol | 1.66 | 68 | 165 | 0.83 |
| 20 | 1,2-5,6-dianhydro-3-methyl dulcitol | 1 | HBr | 1,6-dibromo-1,6-dideoxy-3-methyl-4-acetyl dulcitol | 1.4 | 78 | Oil | 0.58 |
| 21 | 1,2-5,6-dianhydro-3-methyl-4-acetyl dulcitol | 1 | HI | 1,6-diiodo-1,6-dideoxy-3-methyl-4-acetyl dulcitol | 1.8 | 77 | Oil | 0.65 |
| 22 | 1,2-5,6-dianhydro-3-methyl-4- | 1 | HCl | 1,6-dichloro-1,6-dideoxy-3-methyl- | 0.9 | 65 | Oil | 0.52 |

TABLE-continued

| Example | Starting material name | amount (g) | Halogenating agent | Product name | amount (g) | yield (%) | m.p. (°C.) | $R_f$ |
|---|---|---|---|---|---|---|---|---|
| | acetyl dulcitol | | | 4-acetyl dulcitol | | | | |

EXAMPLE 23

1,2-5,6-Dianhydro-3,4-dimethyl dulcitol

A mixture of 14.4 g of 1,6-dibromo-1,6-dideoxy-3,4-dimethoxy dulcitol, 100 ml of water and 100 ml of VARION AD anion exchanger resin in OH[31] form (the resin is a strongly basic polystyrene derivative containing amino groups, manufactured by Nitrokémia Ipartelepek, Balatonfüzfő, Hungary) was stirred for 15 minutes. The ion exchange resin ws filtered off and washed three times with 30 ml portions of distilled water. The aqueous solution was combined with the wash water and evaporated to 40 ml under reduced pressure; the residue was added to the suspension of 1200 ml of ethyl acetate and 120 g of sodium carbonate. The reaction mixture was filtered and the ethyl acetate solution was dried over combusted sodium sulfate, then evaporated to dryness. The residual crude product was recrystalized from hexane, 4.3 g of product were obtained. Yield: 58%. Melting point: 38°–40° C.

EXAMPLE 24

1,2-5,6-Dianhydro-3-methyl dulcitol

A mixture of 13.8 g of 1,6-dibromo-1,6-dideoxy-3-methyl dulcitol, 100 ml of water and 100 ml of VARION AD anion exchange resin in OH− form was stirred for 15 minutes. The ion exchange resin was filtered off and washed three times with 30 ml portions of distilled water. The aqueous solution was combined with the wash water and evaporated to 40 ml under reduced pressure; the residue was added to the suspension of 1200 mll of ethyl acetate and 120 g of sodium carbonate. The reaction mixture was filtered and the ethyl acetate solution was dried over combusted sodium sulfate, then evaporated to dryness. The residual crude product was taken to a silica gel chromatography column having a volume of thirtyfold of the residue and was eluated with a 1 to 1 mixture of benzene and ethyl acetate. 3.6 g of the named product were obtained in pure form. Yield: 52%.

EXAMPLE 25

1,2-5,6-Dianhydro-3-methyl-4-p-phenylbenzoyl dulcitol

1.6 g (0.01 moles) of 1,2-5,6-Dianhydro-3-methyl dulcitol was dissolved in 25 ml of dry benzene and 1.4 ml of dry triethyl amine was added to the solution under stirring. The reaction mixture was heated to 45° C. and a solution of 2.16 g of p-phenylbenzoyl chloride in 5 ml of dry benzene was dropped to it over an hour at the same temperature. The reaction mixture was stirred at 45° C. for half an hour then the precipitated material was filtered off and washed with benzene. The combined benzene solutions were evaporated in vacuo. The residual syrup was taken to a silica gel chromatography column having a volume of thirty times that of the residue and was eluated with a 95 to 5 mixture of benzene and ethyl acetate. Fractions containing the title product were evaporated to dryness and the crystalline residue was recrystallized from ethanol. 1.46 g of product were obtained. Melting point: 75°–78° C. Yield: 43%. $R_f$ is 0.9 (using the same solvent mixture as in Example 1).

What we claim is:

1. 1,2-4,5-dianhydro-3-methyl-xylitol.
2. An anticarcinogenic pharmaceutical composition which comprises a pharmaceutically effective amount of the compound defined in claim 1 along with a pharmaceutically acceptable inert carrier.

* * * * *

UNITED STATES PATENT AND TRADEMARK OFFICE
CERTIFICATE OF CORRECTION

PATENT NO. : 4 337 266
DATED : 29 June 1982
INVENTOR(S) : Ildiko Vidra nee Sandor et al It is certified that error appears in the above-identified patent and that said Letters Patent is hereby corrected as shown below:

In the heading, left column, between items [76] and [21] please insert the following:

-- [73] Assignee: CHINOIN GYÓGYSZER ÉS VEGYÉSZETI TERMÉKEK GYÁRA R.T., Budapest, HUNGARY --.

Signed and Sealed this

First Day of February 1983

[SEAL]

Attest:

GERALD J. MOSSINGHOFF

Attesting Officer

Commissioner of Patents and Trademarks